United States Patent
Takahashi et al.

(10) Patent No.: US 6,615,862 B2
(45) Date of Patent: Sep. 9, 2003

(54) FLOAT FOR LIQUID WASTE DISPOSAL APPARATUS

(75) Inventors: Masao Takahashi, Gunma-ken (JP); Nobuo Murata, Tokyo (JP); Masashi Suzuki, Nagano-ken (JP)

(73) Assignees: Gunma Koike Co., Ltd., Gunma-ken (JP); Koike Medical Co., Ltd., Tokyo (JP); Koshin Chemical Co., Ltd., Tokyo (JP); Showa Jushi Kogyo, Inc., Nagano-ken (JP)

(*) Notice: Subject to any disclaimer, the term of this patent is extended or adjusted under 35 U.S.C. 154(b) by 0 days.

(21) Appl. No.: 09/888,744

(22) Filed: Jun. 27, 2001

(65) Prior Publication Data

US 2002/0023678 A1 Feb. 28, 2002

(51) Int. Cl.⁷ ............................ F16K 31/18; A61M 1/00
(52) U.S. Cl. ........................ 137/433; 137/202; 604/320; 604/323; 73/322.5
(58) Field of Search ................... 73/322.5; 137/192, 137/430, 433, 202; 604/317, 319, 320, 323

(56) References Cited

U.S. PATENT DOCUMENTS

| 5,185,007 A | * | 2/1993 | Middaugh et al. | 604/320 |
| 5,234,419 A | * | 8/1993 | Bryant et al. | 604/320 |
| 5,238,582 A | | 8/1993 | Hori et al. | 210/749 |
| 5,279,602 A | * | 1/1994 | Middaugh et al. | 604/320 |
| 5,284,621 A | * | 2/1994 | Kaufman | 422/32 |
| 5,307,819 A | * | 5/1994 | Trautmann et al. | 604/317 |
| 5,380,308 A | * | 1/1995 | Gunya et al. | 604/323 |
| 5,401,261 A | * | 3/1995 | Gunya et al. | 604/319 |
| 5,507,078 A | * | 4/1996 | Gunya et al. | 604/319 |

FOREIGN PATENT DOCUMENTS

CH  465775  3/1997

OTHER PUBLICATIONS

Patent Abstract of Japan, vol.2000, No.06, Sep. 22, 2000.
Patent Abstract of Japan, vol.1997, No.07, Jul. 31, 1997.

* cited by examiner

Primary Examiner—George L. Walton
(74) Attorney, Agent, or Firm—Townsend & Banta

(57) ABSTRACT

The object of this invention is to provide a float for a liquid waste disposal apparatus having a simple structure for enabling the content inside a container to be easily visually recognizable and allowing a faster and steadier solidification of an absorbed liquid waste. A water-absorptive material 6 is retained inside a spherical float 5 in a manner where a water-absorptive material 6 is wrapped by a water permeable sheet 22 inside a hemispherical primary structural portion 5a and a secondary structural portion 5b capable of being separated into two portions, and thus structured, a circle shaped hole 5c or a square shaped hole 5d of the float 5 serving as a flow path for flowing downward a liquid waste 21 absorbed from an upper portion into a lying member L is formed at the surface of the float 5. The float 5 is contained inside the lying member L in a floatable manner permitted to revolve in a vertical direction.

11 Claims, 11 Drawing Sheets

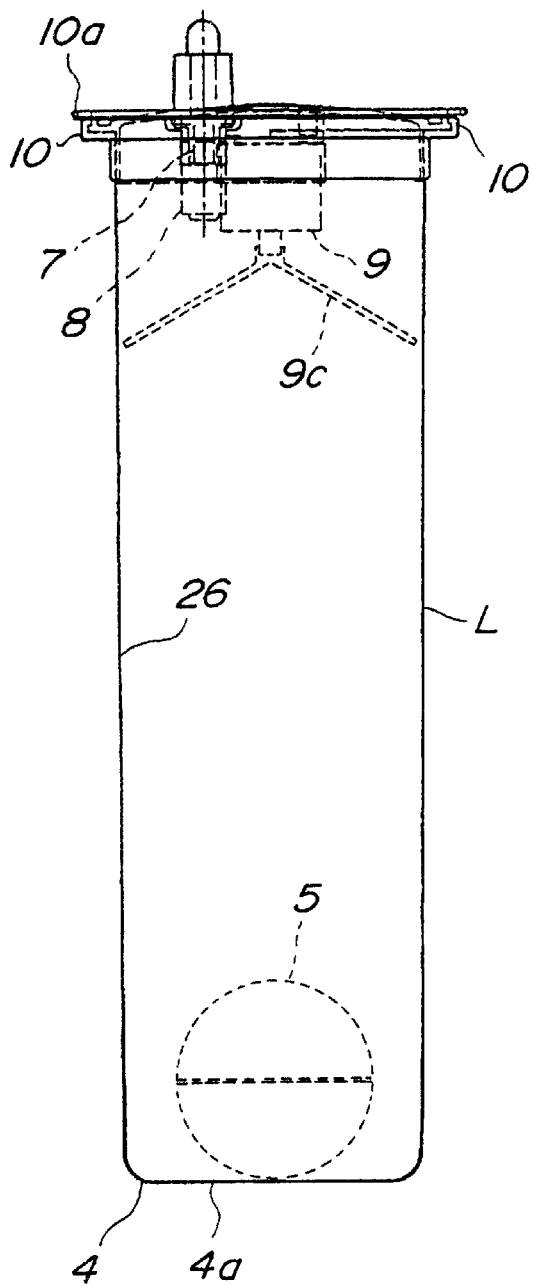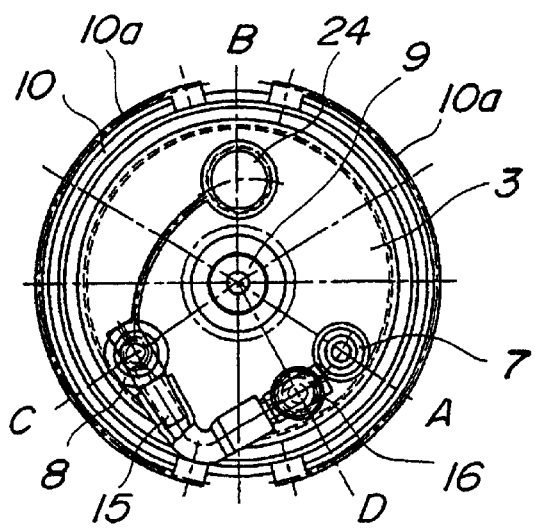

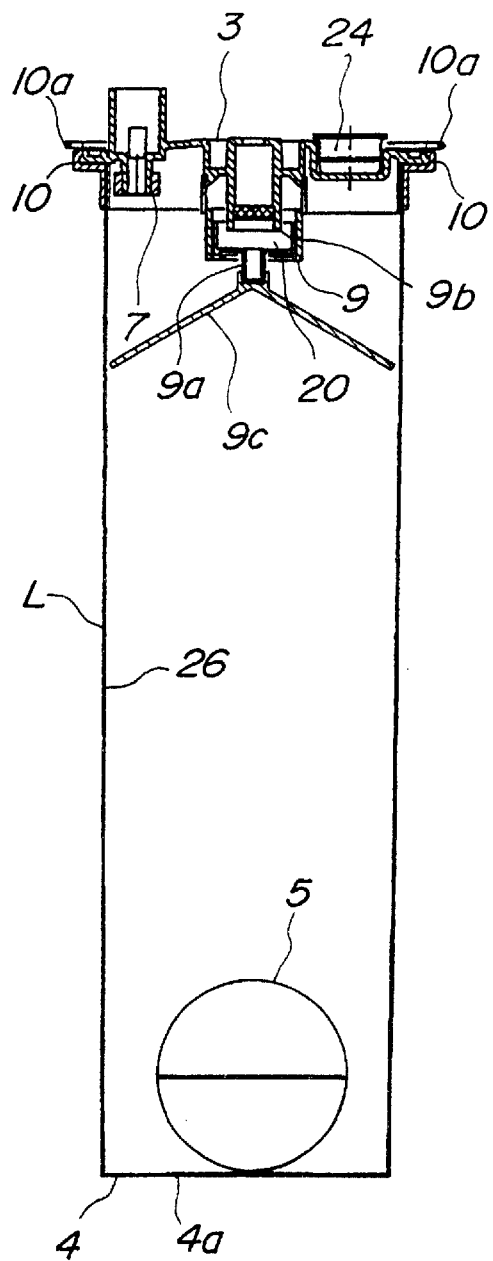
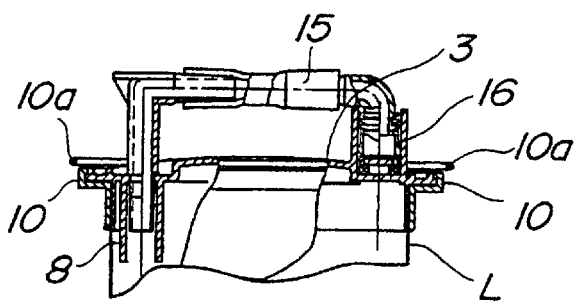
FIG.6(a)
FIG.6(b)

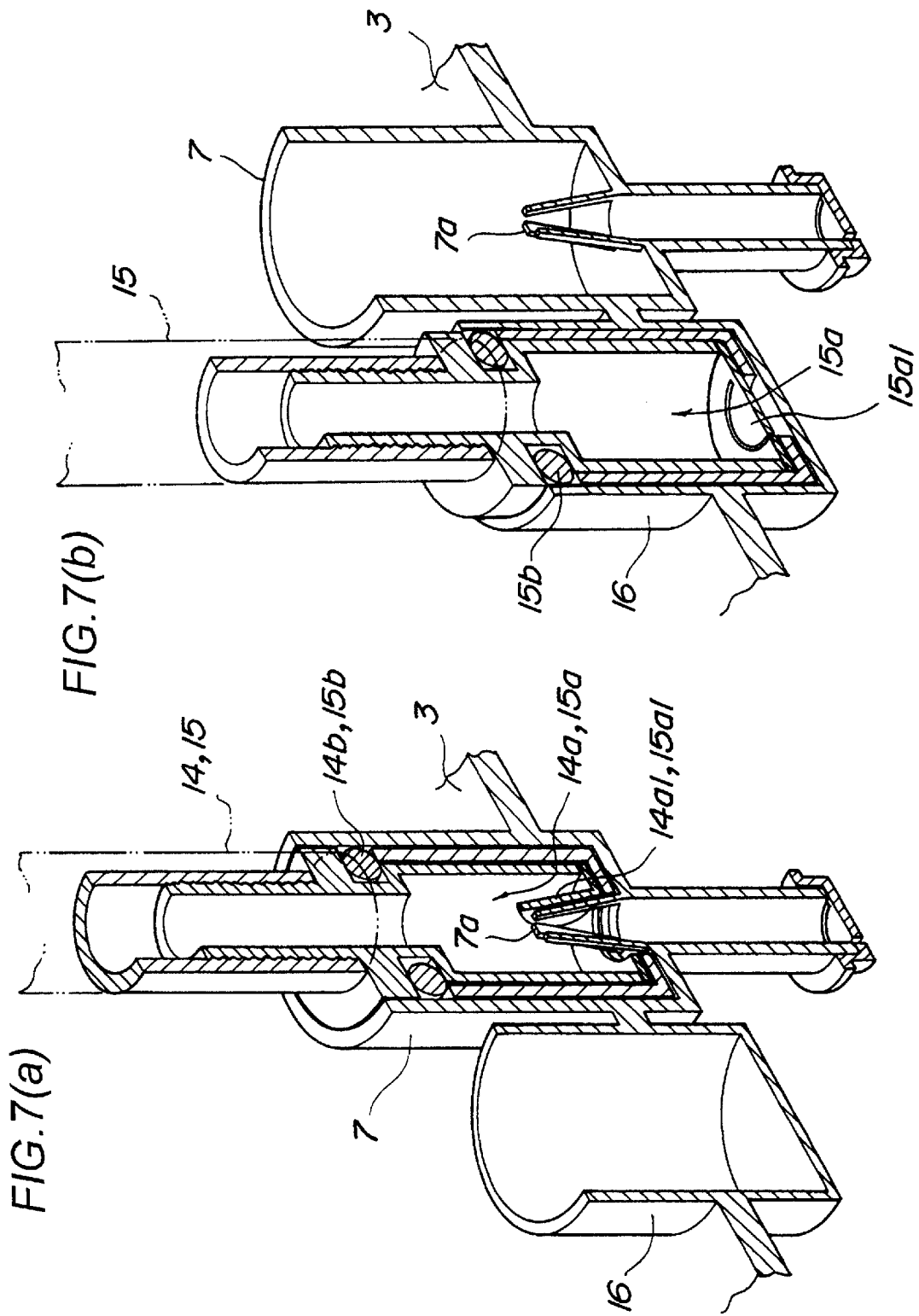

FLOAT FOR LIQUID WASTE DISPOSAL APPARATUS

BACKGROUND OF THE INVENTION

1. Field of the Invention

This invention relates to a float used for a liquid waste disposal apparatus serving to absorb, to solidify and to dispose a liquid waste such as unwanted blood, other body fluids, secretion derived from a medical scene or pus or physiological sodium chloride solution used for cleansing affected areas.

2. Description of Related Art

A liquid waste (e.g. unwanted blood, other body fluids, secretion, pus, or physiological sodium chloride solution used for cleansing affected areas) derived from medical scenes, particularly at a scene of surgical operation, is collected into a container or a collecting bag for disposal and incineration by an absorbing apparatus.

However, since the liquid waste may contain a harmful bacteria or the like, a secondary infection may occur among medical employees, hospital patients and the like, when the container or the collecting bag becomes damaged or when an excessive amount of the liquid waste is absorbed exceeding a capacity of the collecting bag.

For preventing thus created problem, an apparatus for solidifying a liquid waste with a water-absorptive material arranged inside a collecting bag is provided and methods for arranging the liquid waste solidifying water-absorptive material inside the collecting bag are provided such as: a method of forming a collecting bag with a non-water permeable sheet and a water-absorptive sheet stuck with each other in which the water-absorptive sheet is arranged as an inner surface, a method of dropping a prepared water-absorptive material into a collecting bag after an absorption of liquid waste, or a method of fixing a water-absorptive material at a bottom portion of a collecting bag.

Nevertheless, the foregoing conventional example of forming a collecting bag with a non-water permeable sheet and a water-absorptive sheet stuck with each other caused an inner portion to be unable to be seen from outside and also caused difficulty of folding and also caused inconvenience during storage and transport owing to a multiple structure of the collecting bag.

With the foregoing conventional example of dropping a prepared water-absorptive material into a collecting bag after absorption of liquid waste, further absorption could not be performed once solidification is completed and there remained a danger when toppled during the middle of a process since solidification would not proceed until the water-absorptive material is dropped inside the collecting bag.

With the foregoing conventional example of fixing a water-absorptive material at a bottom portion of a collecting bag, a solidifying speed would decrease in association with the proceeding of the liquid waste absorption process.

It is an object of this invention to solve the aforementioned problems by providing a float for a liquid waste disposal apparatus having a simple structure to enable the amount of the content inside a container more visible and to allow a faster and steadier solidification of an absorbed liquid waste.

SUMMARY OF THE INVENTION

This invention for solving the foregoing problems relates to a float for a liquid waste disposal apparatus contained in a floatable state inside a container for containing an absorbed liquid waste comprising: a solidifying agent retained inside; and a flow path for flowing downward the liquid waste absorbed from an upper portion into the container, wherein the float is permitted to revolve in a vertical direction.

Thus structured, the flow path formed by the float flows downward the liquid waste absorbed from the upper portion into the container. The float could bear a simple structure without having any particular means or structures for enabling the float to float steadily since revolution of the float in a vertical direction is permitted. The solidifying agent retained inside the float serves to solidify the liquid waste.

The solidifying agent could be provided within the container since the float itself is capable of retaining the solidifying agent; subsequently, the solidification of liquid waste inside the container enables the container to be solely and sanitarily disposed.

By controlling a specific gravity of the float for a liquid waste disposal apparatus to become less than 1, a liquid surface could be easily confirmed from outside by checking the position of the float since the float would always remain afloat at a gas-liquid interface; accordingly, an amount of the absorbed liquid waste could easily be visually recognized and could also function as a level gauge.

By forming the float into a spherical shape, a disc shape, a circular-donut shape, or with an oval shaped cross section in a longitudinal direction, an elliptical cross section in a longitudinal direction, the float could bear a simple structure capable of maintaining a uniform floating state even when revolving in a vertical direction and thus structured, a relatively large capacity of solidifying agent could be retained inside the float.

The float could bear a simple structure where a floating position could be matched to the position of the absorption stop valve arranged at the upper inner portion of the container by forming a guide member at an outer peripheral portion of a float body in which the guide member is restrained by an inner wall of the container for restricting a floating position of the float in a horizontal direction.

By structuring the float to push upward and activate an absorption stop valve arranged at an upper inner portion of the container, the absorption stop valve is activated to automatically stop absorption when the float inside the container reaches an upper end portion of the container; subsequently, the buoyancy of the float activates the absorption stop valve to automatically stop the absorption of liquid waste before the container becomes full and also serves to prevent an air pump or the like from malfunctioning from an excessive absorption into the container.

By wrapping the solidifying agent retained inside the float with a water permeable sheet (e.g. traditional Japanese paper), the liquid waste absorbed from the upper portion flows downward into the container and permeates into the water penneable sheet (e.g. traditional Japanese paper) via the flow path and contacts to the solidifying agent, or in a state where the liquid waste has flowed through and under the float, the liquid waste permeates into the water permeable sheet (e.g. traditional Japanese paper) and contacts to the solidifying agent; and then, the solidifying agent swells to tear the water permeable sheet causing the solidifying agent from the flow path to be mixed into the liquid waste so as to solidify the liquid waste under the float.

By wrapping the solidifying agent retained inside the float with a water-soluble film, the liquid waste absorbed from the upper portion flows downward into the container via the flow path and contacts to the water-soluble sheet and dissolves the water-soluble sheet, or in a state where the liquid waste has flowed through and under the float, the liquid waste contacts to the water-soluble sheet and dissolves the water-soluble sheet causing the solidifying agent from the flow path to be mixed into the liquid waste so as to solidify the liquid waste under the float.

By having at least one portion of the float for a liquid waste disposal apparatus in a florescent color or in a color distinguishable between a color of a liquid waste, a liquid surface could easily be confirmed from outside since the position of the float could easily be visually recognized; accordingly, an operator could positively confirm the used capacity as well as the remaining capacity of the container.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 5(a) is an outer front view showing a structure of a float for a liquid waste disposal apparatus regarding this invention and a container containing the float; FIG. 5 (b) is an outer plane view showing a structure of a container containing a float for a liquid waste disposal apparatus regarding this invention;

FIG. 6(a) is a cross-sectional view showing B subtracted by A of FIG. 5(b);

FIG. 6(b) is a cross-sectional view showing D subtracted by C of FIG. 5(b);

FIG. 7 is an explanatory view showing a function of a valve member when a connection tube or a patient hose is connected to a closing stopper and an absorption port arranged at a lid of a ceiling portion of a container;

DESCRIPTION OF THE PREFERRED EMBODIMENTS

Figure 1B:
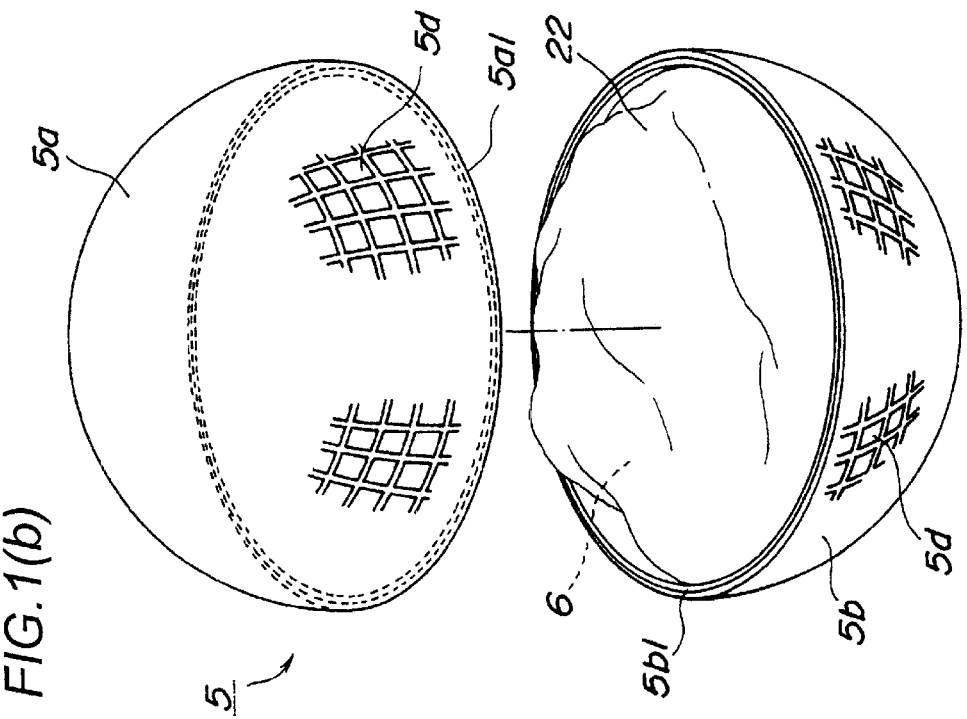
FIG. 1(b) is a perspective explanatory view showing a structure of a second embodiment of a float for a liquid waste disposal apparatus regarding this invention.
Figure 1A:
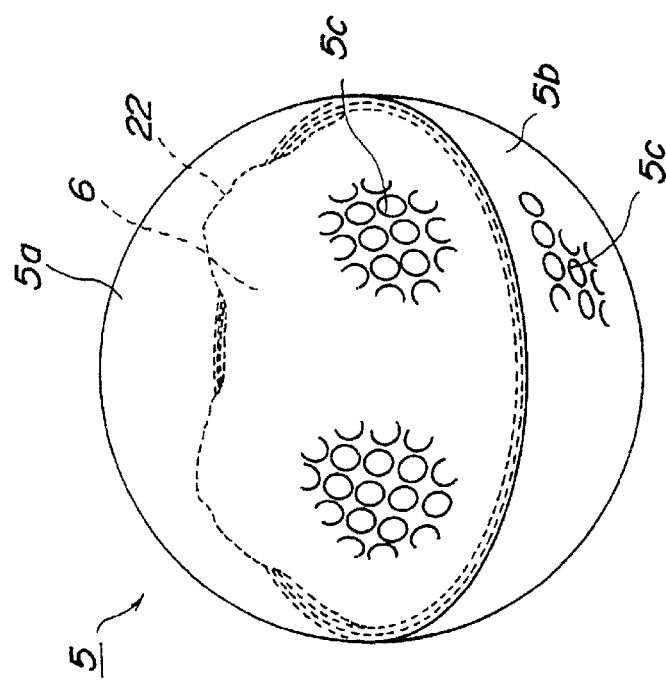
FIG. 1(a) is a perspective explanatory view showing a structure of a first embodiment of a float for a liquid waste disposal apparatus regarding this invention.
Figure 2:
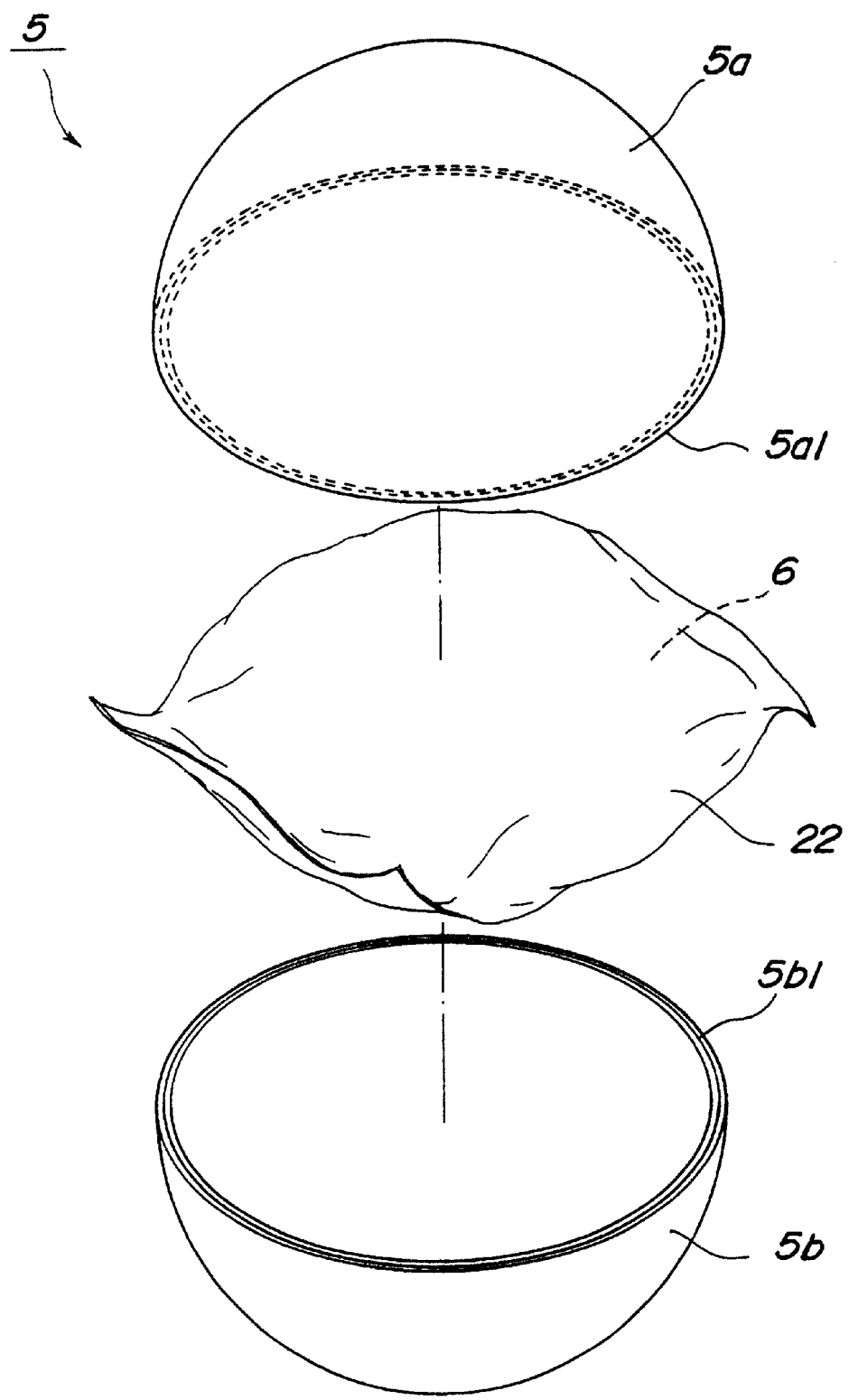
FIG. 2 is an exploded perspective view showing the first and second embodiment of a float for a liquid waste disposal apparatus.

An embodiment of the float for a liquid waste disposal apparatus regarding this invention will hereinafter be described with reference to the drawings. FIG. 1(a) is a perspective explanatory view showing a structure of a first embodiment of a float for a liquid waste disposal apparatus regarding this invention; FIG. 1(b) is a perspective explanatory view showing a structure of a second embodiment of a float for a liquid waste disposal apparatus regarding this invention; and FIG. 2 is an exploded perspective view showing the first and second embodiment of a float for a liquid waste disposal apparatus.

Figure 3:
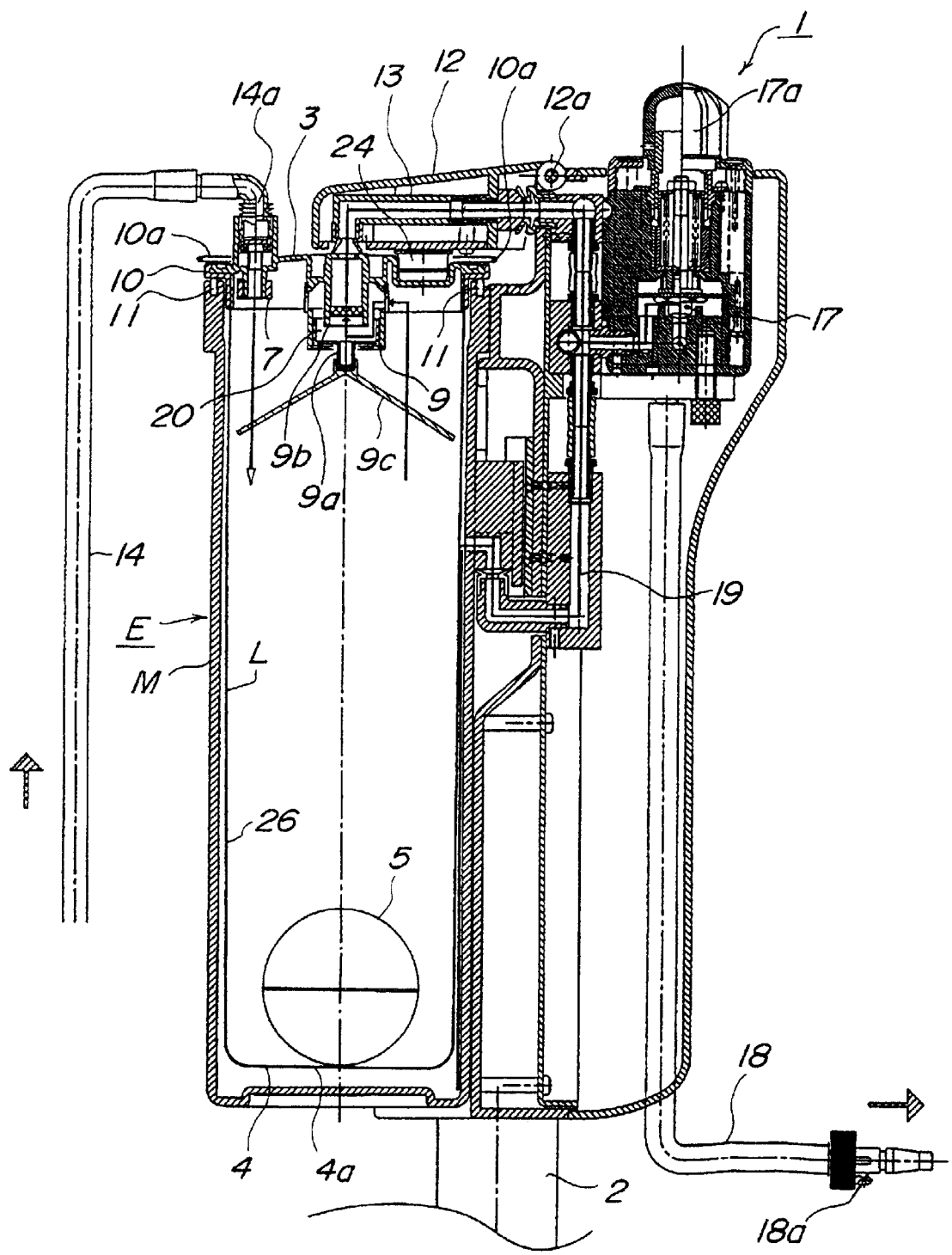
FIG. 3 is a vertical cross-sectional explanatory view showing a structure of a liquid waste disposal apparatus built with a float for a liquid waste disposal apparatus regarding this invention.
Figure 4:
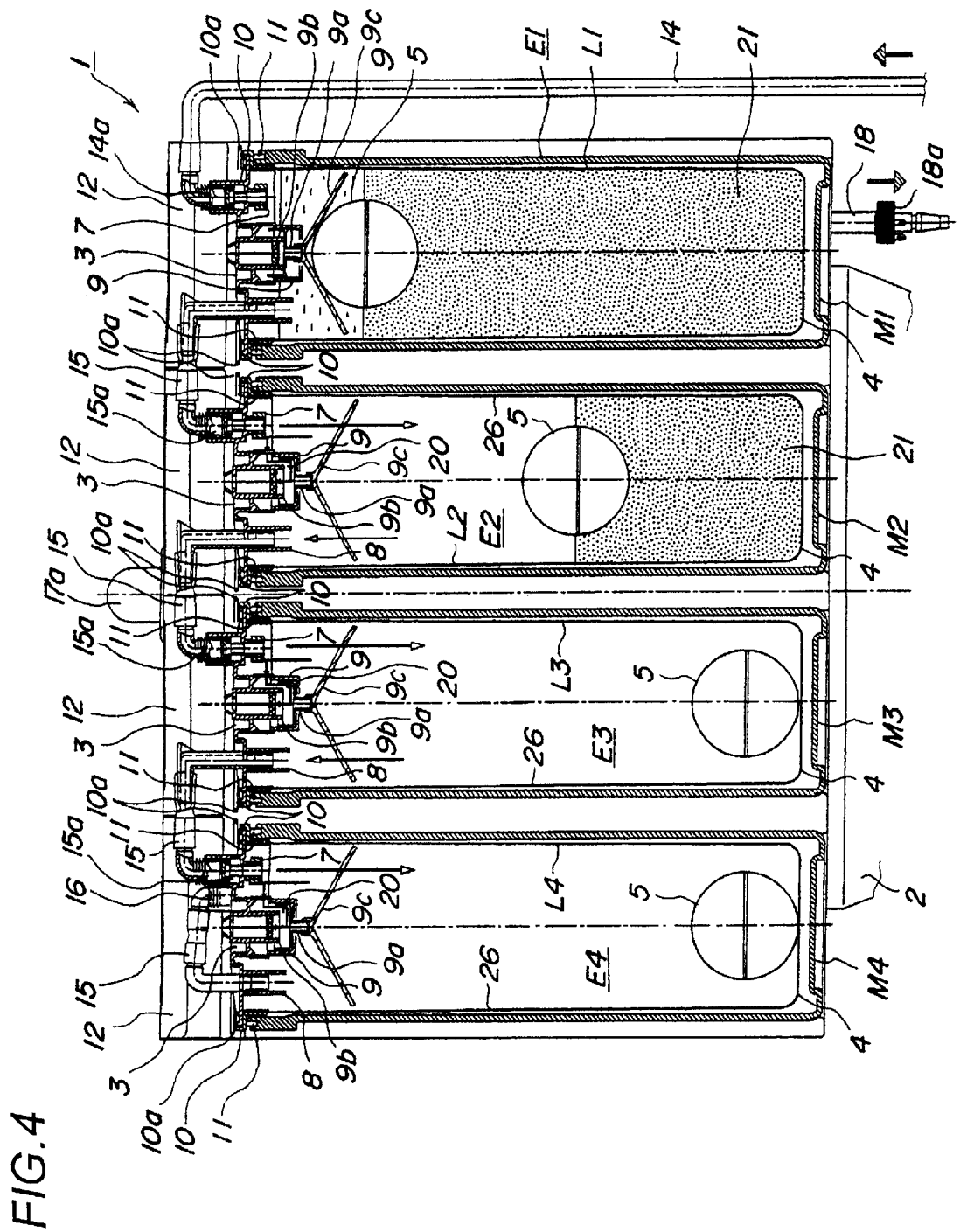
FIG. 4 is a side cross-sectional explanatory view showing a structure of a liquid waste disposal apparatus built with a float for a liquid waste disposal apparatus regarding this invention.

FIG. 3 is a vertical cross-sectional explanatory view showing a structure of a liquid waste disposal apparatus built with a float for a liquid waste disposal apparatus regarding this invention; and FIG. 4 is a side cross-sectional explanatory view showing a structure of a liquid waste disposal apparatus built with a float for a liquid waste disposal apparatus regarding this invention.

FIG. 5(a) is an outer front view showing a structure of a float for a liquid waste disposal apparatus regarding this invention and a container containing the float; FIG. 5(b) is an outer plane view showing a structure of a container containing a float for a liquid waste disposal apparatus regarding this invention; FIG. 6(a) is a cross-sectional view showing B subtracted by A of FIG. 5(b); and FIG. 6(b) is a cross-sectional view showing D subtracted by C of FIG. 5(b).

FIG. 7 is an explanatory view showing a function of a valve member when a connection pipe or a patient hose is connected to a closing stopper and an absorption port arranged at a lid of a ceiling portion of a container.

A structure of the first and second embodiment of the float for a liquid waste disposal apparatus regarding this invention will hereinafter be described with reference to FIG. 1 through FIG. 7.

The embodiment described hereinafter relates to a float for a liquid waste disposal apparatus suitably used for a medical liquid waste disposal apparatus in which a liquid waste 21 (such as dispensable blood, other body fluids, secretion, pus, or physiological sodium chloride solution used for cleansing affected areas produced during operation and treatment) is absorbed and contained inside a lying member L serving as a container contained inside a canister bottle E; wherein the float staying afloat on top of the liquid waste 21 inside the lying member L while mixing a water-absorptive material 6 into the liquid waste 21 so as to solidify the liquid waste 21 for enabling incineration of the lying member L.

As shown in FIG. 1 and FIG. 2, a float 5 for a liquid waste disposal apparatus regarding the first and second embodiment is formed entirely into a spherical shape wherein the float 5 retains within a water-absorptive material 6 serving as a solidifying agent and also has a circle shaped hole 5c or a square shaped hole 5d pierced through the spherical surface to serve as a flow path for flowing downward a liquid waste 21 absorbed from an upper portion into the lying member L.

The float 5 is structured with a primary structural portion 5a and a secondary structural portion 5b capable of being divided into two hemispherical portions wherein the hemispherical primary structural portion 5a and secondary structural portion 5b formed with a polypropylene having a specific gravity less than 1 are engaged to each other by engagement portions 5a1, 5b1 arranged respectively at a peripheral opening portion of the primary structural portion 5a and secondary structural portion 5b. As examples for the engagement portion 5a1, 5b1, an engagement piece and a groove, or a female screw and a male screw could be applied for engagement.

The water-absorptive material 6 (e.g. water permeable polymer) serving as a solidifying agent is contained inside the hemispherical primary structural portion 5a and the secondary structural portion 5b in a manner wrapped inside a water penneable sheet (e.g. traditional Japanese paper) or a water-soluble film. The float 5 is contained inside the lying member L in a floatable manner permitted to revolve in a vertical direction wherein the float 5 has an outer diameter smaller than an inner diameter of the lying member L.

As shown in FIG. 2, in means to contain the water-absorptive material 6 into the float 5, the water-absorptive material is contained into a pouch-like water permeable sheet 22 or a pouch-like water-soluble film in a state where the hemispherical primary structural portion 5a and secondary structural portion 5b of the float 5 are separated and then, the engagement portions 5a1, 5b1 of the hemispherical primary structural portion 5a, secondary structural portion 5b are engaged.

The lying member L has an inner diameter having a prescribed larger length than the outer diameter of the float 5, and thus structured, an interstitial portion is formed between the lying member L and the float 5. The circle shaped hole 5c or the square shaped hole 5d of the float 5 and the interstitial portion between the lying member L and the float 5 serves as a flow path for flowing downward the liquid waste 21 absorbed from the upper portion into the lying member L.

The lying member L containing the float 5 and the absorbed liquid waste 21 has a lid 3 fixed to a ceiling portion; and as shown in FIG. 3 and FIG. 4, thus lying member L is in a detachably contained inside a bottle M serving as an outer container.

As shown in FIG. 4, regarding a liquid waste disposal apparatus 1 of this embodiment, four canister bottles E are connected in series and arranged in a straight line and are supported by a stand 2.

The bottle M serving as an outer container is supported by the stand 2 in a detachable attached manner, and a caster (not shown) is attached to a leg portion of the stand 2. Thus structure allows the stand 2 to steadily move the four canister bottles E in a state where the four canister bottles E are supported and arranged in a straight line.

The bottle M is a transparent plastic cylindrical container having an engagement portion arranged at a rear side for detachably engaging with the stand 2 and a graduation formed at a surface for indicating capacity.

As shown in FIG. 5 and FIG. 6, the lying member L is a united body having a circular plastic lid 3 thermally welded to an opening rim portion of a flexible cylindrical transparent bag 4 form from a low density polyethylene; a plastic ring-shaped holder 10 is engaged and fixed to a peripheral portion of the lid 3.

A path portion of the holder 10 is engaged and fixed to an opening rim portion of the bottle M and a catch 10a is molded to the holder 10 forming a united body.

The canister bottle E containing the lying member L inside the bottle M allows the liquid waste 21 absorbed and contained inside the lying member L to be easily visually recognizable; further, the amount of the liquid waste 21 and a remaining capacity could be confirmed by the graduation formed at the surface of the bottle M.

The float 5 capable of floating is arranged above a bottom portion 4a inside the lying member L in which the float has a specific gravity less than I and retains a water-absorptive material 6 e.g. water-absorptive polymer serving as a solidifying agent inside the cup portion 5b.

As shown in FIG. 4, an absorption port 7 and a discharge port 8 arranged at the lid 3 are liquid-communication to an inside of the lying member L wherein the absorption port 7 absorbs the liquid waste 21 into the lying member L and the discharge port 8 discharges the liquid waste 21 to the absorption port 7 of an adjoining lying member 21.

An exhaust port 9 exhausting air from the lying member 21 for creating a negative pressured state is arranged at a central portion of the lid 3 in an air-communication manner to the inside of the lying member L.

When inserting the lying member L into the bottle M, as shown in FIG. 3 and FIG. 4, a canister head 12 arranged opposite to the stand 2 and pivotally movable around a pivotal movement shaft 12a as a center would pivotally move and open so that the lying members L1, L2, L3, L4 could respectively be inserted into the four bottles M1, M2, M3, M4 fixed to the stand 2 and arranged in a straight line.

As shown in FIG. 3 and FIG. 4, when the lying member L is inserted into the bottle M, a cylindrical portion of the holder engaged to an outer peripheral portion of the lid 3 arranged at the ceiling portion of the lying member L is engagedly inserted to the opening rim portion of the bottle M and thus, a packing II arranged at an opening peripheral rim of the bottle M contacts to a collar portion of the holder 10.

When the canister head 12 is closed by pivotally moving the canister head downward around the pivotal movement shaft 12a as the center, as shown in FIG. 3, an absorption path 13 arranged at the canister head 12 is connected in air-communication with the exhaust port 9 arranged at the lid 3 of the lying member L, and at the same time, the lid 3 of the lying member L is fixed to the bottle M via the holder 10 creating an air-tight sealed state at the space between the bottle M and the lying member L via the packing 11 where the lid 3 and the holder 10 are unitedly pressed against the bottle M fixed by the stand 2.

As shown in FIG. 4, a patient hose 14 is connected to the absorption port 7 arranged at the lid 3 of a primary lying member L1 in a state where a primary canister bottle E1, a secondary canister bottle E2, a third canister bottle E3 and a fourth canister bottle E4 are disposed in a straight line and arranged in an order starting from the primary lying member L1 to the secondary canister bottle E2 to the third canister bottle E3 and to the fourth canister bottle E4; the patient hose 14 is applied to a portion such as an affected portion of a patient so as to absorb the liquid waste 21 such as dispensable blood, other body fluids, secretion, pus, or physiological sodium chloride solution used for cleansing affected areas produced during operation and treatment.

The absorption port 7 arranged at the lid 3 of the secondary lying member L2 is connected to the discharge port 8 arranged at the lid 3 of the primary lying member L1 via a connection pipe 15, and the absorption port 7 arranged at the lid 3 of the third lying member L3 is connected to the discharge port 8 arranged at the lid 3 of the secondary lying member L2 via the connection pipe 15, and the absorption port 7 arranged at the lid 3 of the fourth lying member L4 is connected to the discharge port 8 arranged at the lid 3 of the third lying member L3 via the connection pipe 15.

A closing stopper 16 arranged at the lid 3 of the fourth lying member L4 is connected to the discharge port 8 arranged at the lid 3 of the lying member L4 of the lastly disposed step, that is, the canister bottle E4 via the connection pipe 15; accordingly, the discharge port 8 arranged at the lid 3 of the lying member L4 of the lastly disposed step, that is, the canister bottle E4 becomes closed.

As shown in FIG. 4, an end portion of the connection pipe 15 is connected to the discharge port 8 arranged at the lid 3 of the respective lying member L in a pivotally movable and airtight manner. The pivotally moving the connection pipe 15 around the discharge port 8 as a center allows another end portion of the connection pipe 15 to selectively connect with either the absorption port 7 formed at the lid 3 of a lying member L adjoined downstream (left side of FIG. 4) or the closing stopper 16 of thus lid A valve member 15a is arranged at an opening rim portion of the connection pipe 15 and as shown in FIG. 7(*a*), when connecting the opening rim portion of the connection pipe 15 to the absorption port 7, the connection pipe 15 is in air-communication with the absorption port 7 in which a projecting portion 7a arranged at a surrounding of an opening portion of the absorption port 7 is pushed upward to open a rubber valve 15a1 formed at the valve member 15a and further, a letter O shaped ring arranged at an outer peripheral portion of the valve member 15a is pressingly contacting to an inner wall of an opening portion of the absorption port 7 so as to maintain an airtight state.

As shown in FIG. 7(*b*), when connecting the opening rim portion of the connection pipe 15 to the closing stopper 16, the connection pipe 15 is closed in a state where a letter O shaped ring arranged at an outer peripheral portion of the valve member 15a is pressingly contacting to an inner wall of an opening portion of the closing stopper 16 so as to maintain an airtight state while the rubber valve 15a1 remains shut.

Likewise, a valve member 14a is arranged at an end portion connected to the patient hose 14 on the side of the liquid waste disposal apparatus 1, and in a state where the end portion of the patient hose 14 is connected to the absorption port 7, the patient hose 14 is in air-communication with the absorption port 7 in which a projecting portion 7a arranged at a surrounding of an opening portion of the absorption port 7 is pushed upward to open a rubber valve 14a1 formed at the valve member 14a and further, a letter O shaped ring arranged at an outer peripheral portion of the valve member 14a is pressingly contacting to an inner wall of an opening portion of the absorption port 7 so as to maintain an airtight state.

As shown in FIG. 3, a controller 17 having an adjustment handle 17a for adjusting an absorption pressure (vacuum pressure) is arranged to the stand 2; the controller 17 is connected to a primary absorption hose 18 connected to a terminal takeout port (outlet valve) or an air pump of an absorption piping of a medical gas piping installation in which an adjusted absorbing pressure of the controller 17 causes an inside of the lying member L to become negative pressure via the absorption path 13 and an absorption path 20 of the exhaust port 9.

On the other hand, as shown in FIG. 3, the absorption path 13 is in air-communication with an absorption path 19 in which the absorption path 19 is connected to a gap between the bottle M and the lying member L. Since both an absorption pressure inside the lying member L and an absorption pressure of the gap between the bottle M and the lying member L are negatively pressured with an equal absorption pressure, the air pressure inside and outside of the lying member L arranged inside the bottle M becomes equal and thus, a steady absorption could be performed while maintaining a state shown in FIG. 3 without causing the lying member L formed with a flexible sheet to expand and contract.

An absorption stop valve 9a is arranged at the exhaust port 9 and thus at an inner side of an upper portion of the lying member L; further, attached to a tip of the absorption stop valve 9a is a receiving member 9c. The receiving member 9c of this embodiment has three or more arms extending along a curved surface of a same cone wherein the receiving member 9c guides the float 5 to a center tip portion of the absorption stop valve 9a when the float 5 floats up to an arbitrary horizontal position inside the lying member L.

The receiving member 9c could be structured as a cone shaped member having numerous holes or structured as a net having a conical shape. Furthermore, a parasol shaped receiving member 9c having a curvature radius larger than that of the spherical float 5 could be adopted, or a net-like member arranged in a horizontal direction, or a flat board-like member having numerous holes could be adopted.

As shown by the canister bottles E2, E3, E4 of FIG. 4, a self-weight of the absorption stop valve 9a and the receiving member 9c allows the absorption stop valve 9a arranged at the inner upper portion of the lying member L to maintain a downward position until the float 5 floats to reach the ceiling portion and subsequently, the absorption path 20 in air-communication with the absorption path 13 from inside the lying member L could be maintained.

On the other hand, as shown by the canister bottle E1 of FIG. 4, when the liquid waste 21 is absorbed into the lying member L to elevate the float 5 until the float 5 reaches the ceiling portion of the lying member L, the float 5 guided to a center position by the receiving member 9c pushes the absorption stop valve 9a and the receiving member 9c upward against the self-weight of the absorption stop valve 9a and the receiving member 9c and causes the absorption path 20 in air-communication with the absorption path 13 from inside the lying member L to become closed.

Once the absorption stop valve 9a is pushed upward to close the absorption path 20, owing to an absorbing strength of exhaust, the absorption stop valve 9a adheres to a cylindrical body 9b arranged above so as to maintain the closed state of the absorption path 20.

The float 5 shown in FIG. 1 and FIG. 2 is placed on the bottom portion 4a of the lying member L, and as shown in FIG. 4, the liquid waste 21 is guided below the float 5 via a flow path comprised of the circle shaped hole 5c or the square shaped hole 5d of the float 5 or the interstitial portion formed between the float 5 and the inner wall 26 of the lying member L when the liquid waste 21 flows into the lying member L from the upper portion; subsequently, the float 5 stays afloat at liquid-gas interface of the liquid waste 21 since the float 5 is structured to have a specific gravity less than 1.

The liquid waste 21 absorbed into the lying member L from the absorption port 7 comes around to a bottom portion via the circle shaped hole 5c or the square shaped hole 5d of the float 5 or the interstitial portion formed between the float 5 and the inner wall 26 of the lying member L; then the liquid waste 21 permeates through the water permeable sheet 22 (e.g. traditional Japanese paper) contained within the float 5 having a water-absorptive material 6 wrapped inside; then the liquid waste 21 contacts to the water-absorptive material 6 so that the water-absorptive material 6 would swell to tear the water permeable sheet 22 and dissolve into the liquid waste 21 contained inside the lying member L to solidify the liquid waste 21 into a gel, or otherwise, the liquid waste 21 contacts to the water-soluble film contained within the float 5 having a water-absorptive material 6 wrapped inside; then the liquid waste 21 dissolves the water-soluble film so that the water-absorptive material 6 dissolve into the liquid waste 21 contained inside the lying member L to solidify the liquid waste 21 into a gel.

Hereinafter an operating procedure and an operation of the liquid waste disposal apparatus 1 shall be described. The lying member L is preserved and transported in a state where the holder 10 remains attached by a method such as sealing the lying member L with a vinyl-wrapping container. In thus situation, the catch 10a arranged at the holder 10 could be laid down to both sides of the lid 3, and the lying member L could be preserved and transported in a relatively compact manner since the lying member L itself is flexible.

At a time for operation, the lying member L is prepared in correspondence with the number of the bottle M arranged in a straight line at the stand 2, and then, the adjustment handle 17a is turned to a prescribed direction shown in FIG. 3 so as to turn the controller 17 off, and then an adapter 18a of the primary absorption hose 18 is connected to a terminal takeout port or an air pump of a medical gas piping installation (not shown).

Next, the canister bottle 12 of the stand 2 is opened to insert the lying member L into all of the bottles M, and then, the connection pipe 15 rotatively attached to the discharge port 8 formed at the lid 3 of the ceiling portion of the respective lying members L is inserted and connected to the absorption port 7 formed at the lid 3 of the ceiling portion of the lying member L adjoined to the left side in FIG. 4.

The end portion on the side of the valve member 14a of the patient hose 14 is inserted and connected to the absorption port 7 formed at the lid 3 of the ceiling portion of the lying member L1 of the primary canister bottle E1 and further, in means for closure, the closing stopper 16 formed at the lid 3 of the lying member L4 is connected to the connection pipe 15 in which the connection pipe 15 is connected to the discharge port 8 formed at the lid 3 of the lying member L4 of the last and fourth canister bottle E4.

Next, the canister head 12 is closed and locked to the stand 2. Before the beginning of absorption, the float 5 is arranged at the bottom portion 4a of the lying member L as shown in FIG. 3 owing to the weight of the float 5 itself.

Then, the adjustment handle 17a of the controller 17 is turned to turn the controller 17 for adjusting to a prescribed absorption pressure. In thus case, the negative pressure of the primary absorption hose 18 causes the inside of the lying member L to become negative pressure via the absorption path 13 formed at the respective canister heads 12 and the absorption path 20 of the exhaust port 9 formed at the lid 3 of the ceiling portion of the respective lying members L; further, the gaps between the respective bottles M and the respective lying members L are also caused to become negative pressure via the absorption path 19 in air-communication with the gaps between the respective bottles M and the respective lying members L.

In this process, the presence of absorption pressure inside the lying member L is to be confirmed by closing a tip of the patient hose 14 and whether or not the lying member L inflates along the bottle M is also to be confirmed.

When an absorption of the liquid waste 21 is started after a tip of the patient hose 14 is applied to such as an affected area of the patient, as shown in FIG. 4, the liquid waste 21 from the patient hose 14 is guided into the lying member L via the absorption port 7 formed at the lid 3 of the lying member L1 of the primary canister bottle E1.

The liquid waste 21 absorbed into the lying member L1 reaches below the float 5 via the interstitial portion formed between the lying member L1 and the float 5 or via the circle shaped hole 5c or the square shaped hole 5d of the float 5.

Since the float 5 has a specific gravity less than the float 5, the float maintains a position at the level of the liquid waste 21 and stays afloat at liquid-gas interface; thus, the liquid waste 21 permeates through the water permeable sheet 22 contained within the float 5 and wrapping the water-absorptive material 6 inside, and then contacts to the water-absorptive material 6 so that the water-absorptive material 6 would swell to tear the water permeable sheet 22 and spread among the liquid waste 21 and solidify the liquid waste 21 into a gel; or otherwise, the water-soluble film contained within the float 5 and wrapping the water-absorptive material 6 inside dissolves so that the water-absorptive material 6 would spread among the liquid waste 21 to solidify the liquid waste 21 into a gel.

Even after the progress of the absorption of the liquid waste 21, the water-absorptive material 6 could effectively spread among the liquid waste 21 absorbed afterwards and solidify thus liquid waste 21 into a gel since the float 5 constantly stays afloat at the liquid-gas interface.

Further, since the float 5 constantly stays afloat at the liquid-gas interface, the amount of the absorbed liquid waste 21 could easily be visually recognized so that the float 5 could function as a level gauge as well. Therefore, it is suitable to have a least one portion of the float 5 to be molded with a material having a color distinguishable with the color of the liquid waste 21 or a distinguishing color such as a florescent color.

As shown in FIG. 4, as the absorption process of the liquid waste 21 progresses, the float 5 elevates to the ceiling portion of the lying member L and is guided by the receiving member 9c and then, the buoyancy of the float 5 pushes the absorption stop valve 9a and the receiving member 9c upward against the self weight of the absorption stop valve 9a and the receiving member 9c so that the absorption path 20 becomes closed and the absorption pressure from the exhaust port 9 would cease, as a manner shown as primary canister bottle E1 of FIG. 4.

With the cease of the absorption pressure inside the lying member L1, an absorption pressure of the L2 adjoined at the left side of the lying member L1 in FIG. 4 affects the inside of the lying member L1 via the absorption path 13 of the stand 2, the absorption path 20 of the exhaust port 9 of the lying member L2, the absorption port 7 of the lying member L2, the connection pipe 15, the discharge port 8 of the lying member L1; the not-yet gelled liquid waste 21 absorbed above the float 5 inside the lying member L1 is absorbed into the lying member L2 via the discharge port 8 of the lying member L1, the connection pipe 15 and the absorption port of the lying member L2.

In the same manner as the foregoing lying member L1, the float 5 elevates and stays afloat at the level of the liquid waste 21 in correspondence with the rise in the level of the liquid waste 21 contained inside the lying member L2, and when the float 5 reaches the ceiling portion of the lying member L2, the float 5 is guided by the receiving member 9c and the buoyancy of the float 5 pushes the absorption stop valve 9a and the receiving member 9c upward to close the absorption path 20 and cease the absorption pressure of the lying member L2.

Likewise, an absorption pressure of the lying member L3 adjoined to the lying member L2 absorbs the absorbed liquid waste 21 contained above the float 5 of the lying member L2 into the lying member L3 via the discharge port 8 of the lying member L2, the connection pipe 15 and the absorption port of the lying member L3.

In the same manner as the foregoing lying members L1, L2, the float 5 elevates and stays afloat at the level of the liquid waste 21 in correspondence with the rise in the level of the liquid waste 21 contained inside the lying member L3, and when the float 5 reaches the ceiling portion of the lying member L2, the float 5 is guided by the receiving member 9c and the buoyancy of the float 5 pushes the absorption stop valve 9a and the receiving member 9c upward to close the absorption path 20 and cease the absorption pressure of the lying member L3.

Likewise, an absorption pressure of the lying member L4 adjoined to the lying member L3 absorbs the absorbed liquid waste 21 contained above the float 5 of the lying member L3 into the lying member L4 via the discharge port 8 of the lying member L3, the connection pipe 15 and the absorption port of the lying member L4.

In the same manner as the foregoing lying members L1, L2, L3, the float 5 elevates and stays afloat at the level of the liquid waste 21 in correspondence with the rise in the level of the liquid waste 21 contained inside the lying member L4, and when the float 5 reaches the ceiling portion of the lying member L4, the float 5 is guided by the receiving member 9c and the buoyancy of the float 5 pushes the absorption stop valve 9a and the receiving member 9c upward to close the absorption path 20 and cease the absorption pressure of the lying member L4.

Therefore, since the buoyancy of the float 5 upwardly pushes and activates the absorption stop valve 9a, the absorption of the liquid waste 21 is automatically ceased before all of the lying members L become full with liquid waste 21; accordingly, the air-pump or the like would not malfunction due to an excessive absorption into the respective lying members L.

After the use of the liquid waste disposal apparatus, the lying member L is taken out from the bottle M by opening the canister head 12 of the stand 2, and then, an end portion of the connection pipe 15 is inserted and connected to the absorption port 7 arranged at the lid 3 wherein another end-portion of the connection pipe is rotatively connected to the discharge port 8 of the lid 3 of the respective lying members L, and then, as shown in FIG. 3, FIG. 5(b) and FIG. 6(a), a cap 24 prearranged to the lid 3 covers the exhaust port 9 arranged at the lid 3 of the respective lying members L for hermetically sealing the lying members L, and subsequently, pulling out the lying member L with the catch 10a of the holder 10 enables easy detachment from the bottle M so that the lying member L could solely be disposed for incineration and the like.

Further, the lying member could be solely stood upright owing to a function of the bottom portion 4a of the lying member L in a state where the liquid waste 21 inside the lying member L is gelled by the water-absorptive material 6.

The liquid waste 21 remaining inside the connection pipe 15 or the patient hose 14 would not drip down during a detachment of the patient hose 14 or the connection pipe 15 from the absorption port 7 owing to a function of the rubber valves 14a1, 15a1 of the valve members 14a, 15a of the connection pipe 15 or the patient hose 14.

Thus structured, the liquid waste 21 absorbed from an upper portion flows into the lying member L and down under the float 5 via the flow path e.g., the circle shaped hole 5c or the square shaped hole 5d. The float 5 could bear a simple structure without having any particular means or structures for enabling the float 5 to float steadily since revolution of the float 5 in a vertical direction is permitted. The water-absorptive material 6 retained inside the float 5 serves to solidify the liquid waste 21.

The water-absorptive material 6 is retained by the float 5 itself so that the water-absorptive material 6 could be contained inside the lying member L; subsequently, the liquid waste 21 inside the lying member L could be solidified for enabling the lying member L to be solely and sanitarily disposed.

The float 5 could always remain afloat at the liquid-gas interface by structuring the float 5 to have a specific gravity less than 1; accordingly, the position of a liquid-level could easily be confirmed from outside by confirming the position of the float 5, and further, the amount of the absorbed liquid waste 21 could easily be visually recognized so that the float 5 could also function as a level gauge.

By forming the float 5 into a spherical shape, the float 5 could bear a simple structure capable of maintaining a uniform floating state even when revolving in a vertical direction and thus structured, a relatively large capacity of solidifying agent could be retained inside the float 5.

By structuring the float 5 to push upward and activate an absorption stop valve 9a arranged at an inner side of an upper portion of the lying member L, the absorption stop valve 9a is activated to automatically stop absorption when the float 5 inside the lying member L reaches an upper end portion of the lying member L; subsequently, the buoyancy of the float 5 activates the absorption stop valve 9a to automatically stop the absorption of liquid waste 21 before the lying member L becomes full and also serves to prevent an air pump or the like from malfunctioning from an excessive absorption into the container.

By wrapping the water-absorptive material 6 retained inside the float 5 with a water permeable sheet 22 (e.g. traditional Japanese paper), the liquid waste 21 absorbed from the upper portion flows downward into the lying member L and permeates into the water permeable sheet 22 (e.g. traditional Japanese paper) via the circle shaped hole 5c or the square shaped hole 5d and contacts to the water-absorptive material 6, or in a state where the liquid waste 21 has flowed through and down under the float 5, the liquid waste 21 permeates into the water permeable sheet 22 (e.g. traditional Japanese paper) and contacts to the water-absorptive material 6; and then, the water-absorptive material 6 swells to tear the water permeable sheet 22 causing the water-absorptive material 6 from the circle shaped hole 5c or the square shaped hole 5d to be mixed into the liquid waste 21 so as to solidify the liquid waste 21 under the float 5.

By wrapping the water-absorptive material 6 retained inside the float 5 with a water-soluble film, the liquid waste 21 absorbed from the upper portion flows downward into the lying member L via the circle shaped hole 5c or the square shaped hole 5d and contacts to the water-soluble sheet and dissolves the water-soluble sheet, or in a state where the liquid waste 21 has flowed through and down under the float 5, the liquid waste 21 contacts to the water-soluble sheet and dissolves the water-soluble sheet causing the water-absorptive material 6 from the circle shaped hole 5c or the square shaped hole 5d to be mixed into the liquid waste 21 so as to solidify the liquid waste 21 under the float 5.

By forming at least one portion of the float 5 into a florescent color or a color distinguishable from the liquid waste 21, the position of the float 5 could easily be visually recognized from outside so that the liquid-surface could easily be recognized and thus, the operator could positively confirm the used state and the remaining capacity of the lying member L.

The liquid waste 5 contained above the float 5 could be guided to the adjoining lying member L in a liquid state without being solidified, and further, the disposal capacity could be easily increased by consecutively connecting numerous lying members L, as shown in FIG. 4.

Although the float 5 of the foregoing embodiment is formed from a polypropylene material having a specific gravity less than 1, as long as the specific gravity of the float 5 is less than 1, the material is not to be limited to polypropylene.

The holes formed at the surface of the float 5 serving as the flow path could be shaped other than a circle or a square, and could be formed having a net-like structure.

As examples regarding the retaining means for retaining the water-absorptive material 6 inside the float 5, the water permeable sheet 22 (e.g. traditional Japanese paper) or the water-soluble film wrapping inside the water-absorptive material 6 are described above, however, other means for retaining the water-absorptive material 6 could be used such as a means by solidifying the water-absorptive material 6 with a water-dissolvable filling material, a means by retaining with a water-decomposable non-fabric paper or a non-fabric cloth.

Figure 8A:
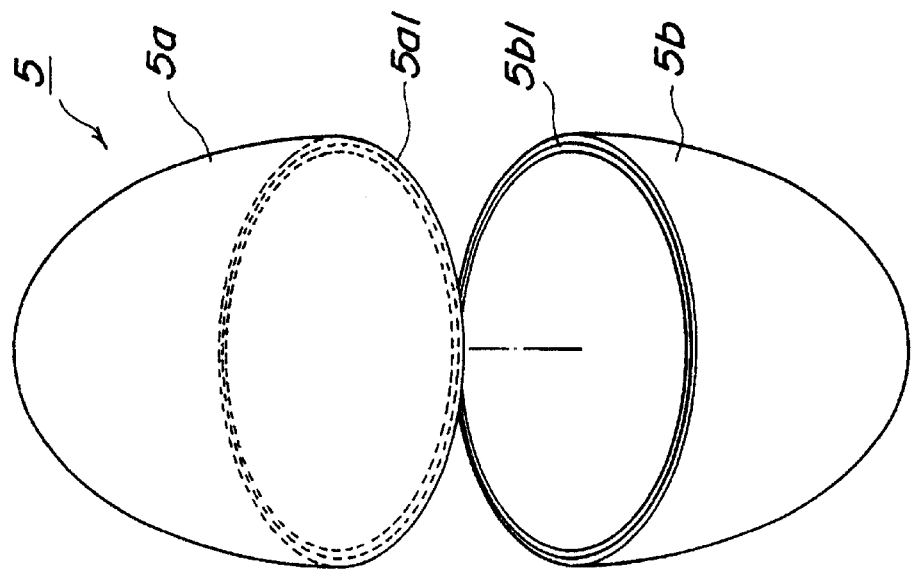
FIGS. 8(a) and (b) are perspective explanatory views showing a structure of the third and fourth embodiment of the float for a liquid waste disposal apparatus regarding this invention.

A third, fourth, fifth and sixth embodiment of the float for a liquid waste disposal apparatus regarding this invention will hereinafter be described with reference to the FIG. 8 and FIG. 9. FIGS. 8(a) and (b) are perspective views showing the structures of the third and fourth embodiment of the float for a liquid waste disposal apparatus regarding this invention. FIGS. 9(a) and (b) are perspective views showing the structures of the third and fourth embodiment of the float for a liquid waste disposal apparatus regarding this invention. The symbols of the components having the same structure as the first and second embodiment shall be indicated using the same symbols.

FIGS. 8(a) and (b) are views of the third and fourth embodiment showing the float 5 having a structure capable of being separated into two portions in a latitudinal direction comprised of the primary structural portion 5a and the secondary structural portion 5b, and the float 5 having a cross section with an elliptical shape or an oval shape. In the same manner as the foregoing embodiments, the primary structural portion 5a and the secondary structural portion 5b are separated to contain the water permeable sheet 22 and the water-soluble film for wrapping inside the water-absorptive material serving as a solidifying agent; and subsequently the engagement portions 5a1, 5b1 are engaged.

FIGS. 9(a) and (b) are views of the fifth and sixth embodiment showing the float 5 having a structure capable of being separated into two portions comprised of the primary structural portion 5a and the secondary structural portion 5b at the outer diameter portion of the float 5, and the float having a disc shape or a circular-donut shape. In the same manner as the foregoing embodiments, the primary structural portion 5a and the secondary structural portion 5b are separated to contain the water permeable sheet 22 and the water-soluble film for wrapping inside the water-absorptive material serving as a solidifying agent; and subsequently the engagement portions 5a1, 5b1 are engaged.

Figure 8B:
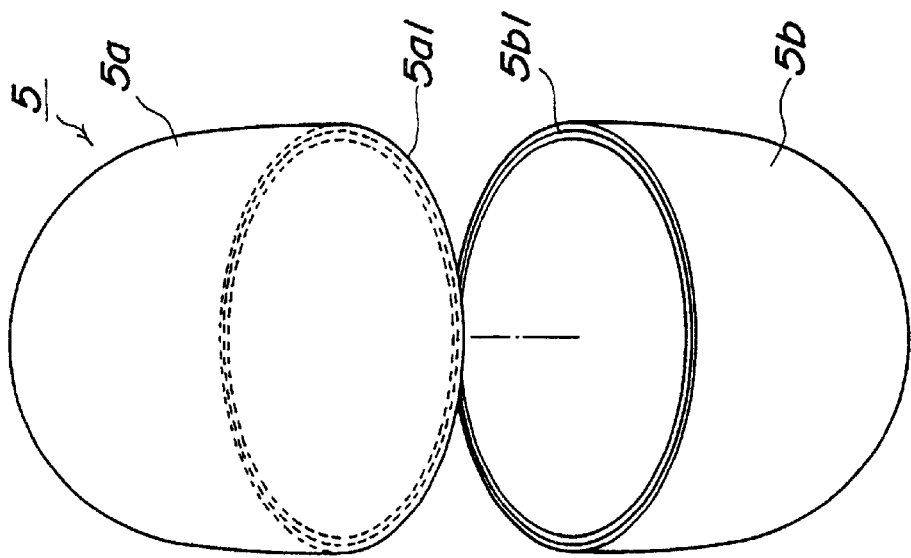
Figure 9B:
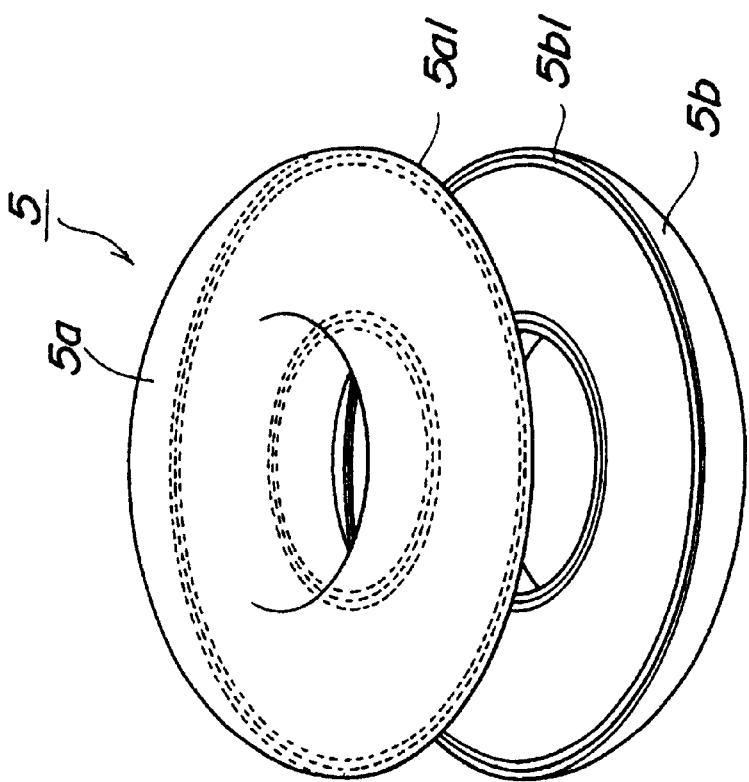
FIGS. 9(a) and (b) are perspective explanatory views showing a structure of a fifth and sixth embodiment of the float for a liquid waste disposal apparatus regarding this invention.
Figure 9A:
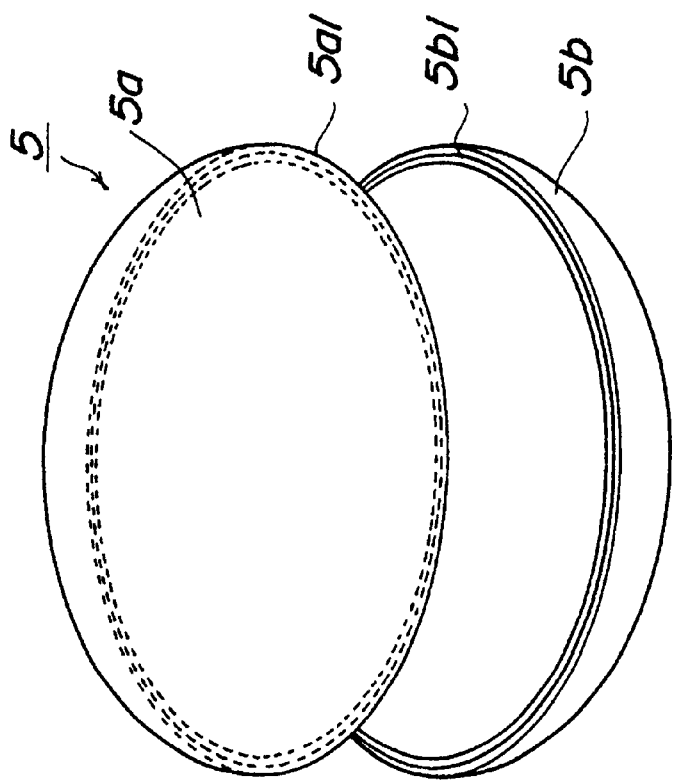

The float 5 of the third through sixth embodiment shown in FIG. 8 and FIG. 9 is contained to float inside the lying member L in a state being permitted to revolve in a vertical direction, and in the same manner as the first and second embodiment, the circle shaped hole 5c, the square shaped hole 5d or the like serving as the flow path are formed at the surface of the float 5.

The float 5 of the third through sixth embodiment elevates to float at the level of the liquid waste 21 and when the float 5 reaches the ceiling portion of the lying member L, the float 5 is guided by the receiving member 9c and the buoyancy of the float 5 pushes the absorption stop valve 9a and the receiving member 9c upward to close the absorption path 20 and to cease the absorption pressure of the lying member L. The other structural portions have the same structure and effect as that of the first and second embodiment.

A seventh and eighth embodiment of the float for a liquid waste disposal apparatus regarding this invention will hereinafter be described with reference to the FIG. 10 and FIG. 11. FIGS. 10(a) and (b) are perspective explanatory views showing the structures of the seventh and eighth embodiment of the float for a liquid waste disposal apparatus regarding this invention. FIG. 11 is vertical cross sectional view showing the structure of the liquid waste disposal apparatus used for the float for the liquid waste disposal apparatus regarding the seventh and eighth embodiment. The symbols of the components having the same structure as the first and second embodiment shall be indicated using the same symbols.

FIGS. 10(a) and (b) are views of the seventh and eighth embodiment showing the float 5 structured with the hemispherical primary structural portion 5a and the secondary structural portion 5b wherein the secondary structural portion 5b comprising one of the two hemispherical portions has a guide member 31 arranged at an outer peripheral opening portion having an outer diameter in correspondence with the inner diameter of the lying member L.

FIG. 10(a) is a view of the seventh showing the guide member 31 structured with an annular body wherein the guide member 31 and the secondary structural portion 5b are connected by a plurality of connecting plates 31a. An interstitial portion is formed between the secondary structural portion 5b and the annular body so as to serve as a flow path.

Figure 10B:
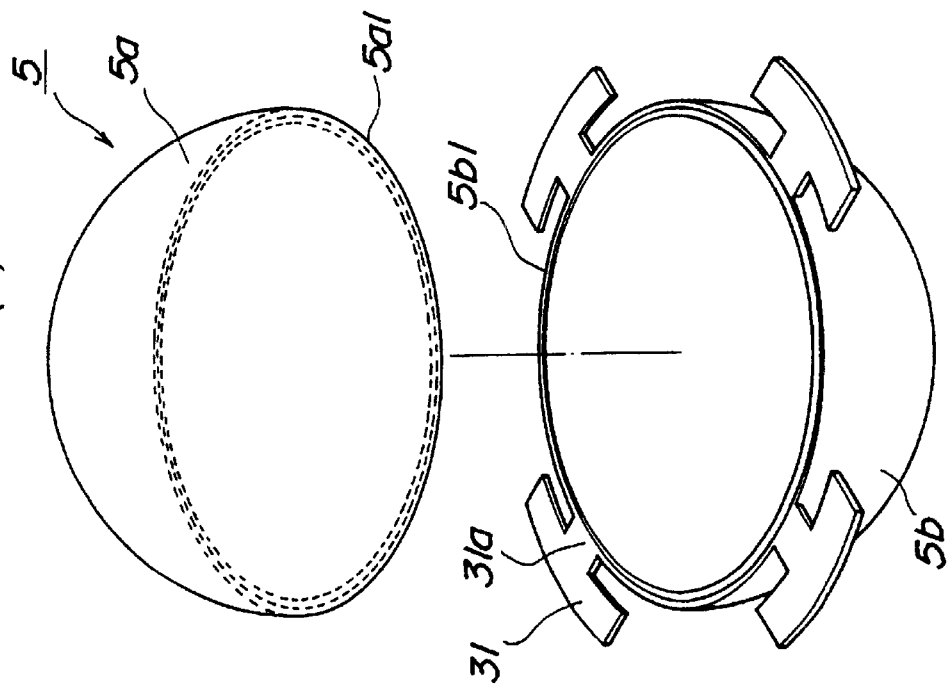
FIGS. 10(a) and (b) are perspective explanatory views showing a structure of a seventh and eighth embodiment of the float for a liquid waste disposal apparatus regarding this invention.
Figure 10A:
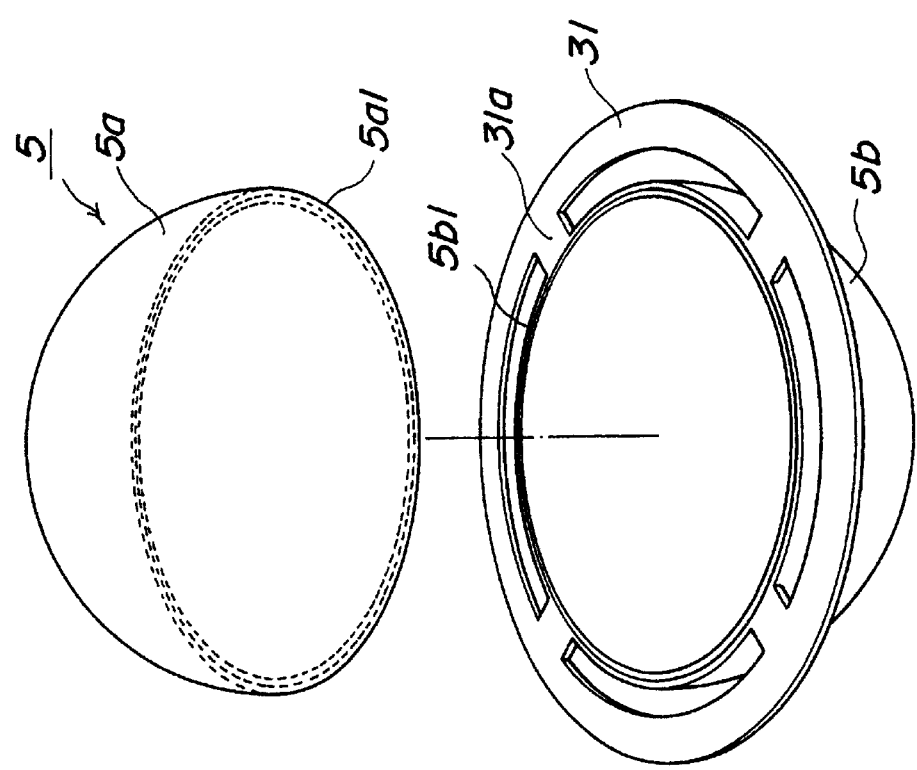
Figure 11:
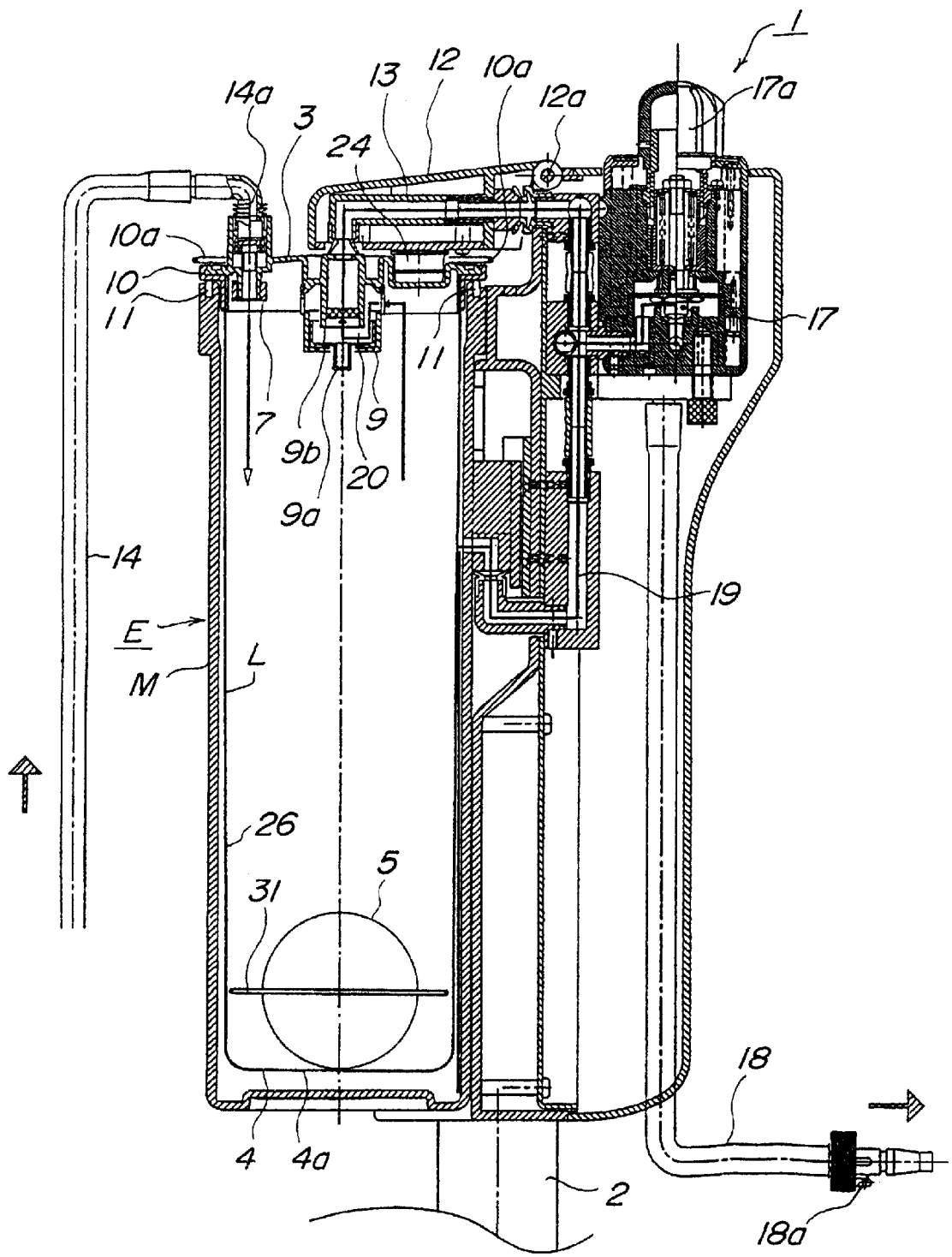
FIG. 11 is a vertical cross sectional view showing a structure of a liquid waste disposal apparatus used for the float for a liquid waste disposal apparatus regarding the seventh and eighth embodiment.

FIG. 10(b) is a view of the eighth embodiment showing the guide member 31 in accordance with the seventh embodiment shown in FIG. 10(a) having an annular body in a state separated into four portions; thus structured, the cost for the material of the float 5 could be reduced and the downward flow of the liquid waste 21 could be accelerated by enlarging the interstitial portion formed between the secondary structural portion 5b and the annular body for serving as a flow path.

FIG. 11 is a view of the seventh and eighth embodiment showing the float 5 structured with the guide member 3 restrained by the inner wall 26 of the lying member L for restricting the floating position of the float 5 in a horizontal direction wherein the float 5 is capable of floating steadily to the upward pushing position of the absorption stop valve 9a without having to arrange the receiving member 9c attached to the tip of the absorption stop valve 9a of the foregoing embodiments.

The float 5 of the seventh and eighth embodiment shown in FIGS. 10(a) and (b) is contained to float inside the lying member L in a state being permitted to revolve in a vertical direction, and in the same manner as the first and second embodiment, the circle shaped hole 5c, the square shaped hole 5d or the like serving as the flow path are formed at the surface of the float 5.

The float 5 of the seventh and eighth embodiment elevates to float at the level of the liquid waste 21 and when the float 5 reaches the ceiling portion of the lying member L, the float 5 is guided by the receiving member 9c and the buoyancy of the float 5 pushes the absorption stop valve 9a and the receiving member 9c upward to close the absorption path 20 and to cease the absorption pressure of the lying member L. The other structural portions have the same structure and effect as that of the first and second embodiment.

This invention having the aforementioned structure and effect enables the content inside a container to be easily visually recognizable and allows a faster and steadier solidification of an absorbed liquid waste by having a simple structure.

In respect of the thus structured float for a liquid waste disposal apparatus regarding this invention, the flow path formed by the float flows downward a liquid waste absorbed from an upper portion into the container. The float could bear a simple structure without having any particular means or structures for enabling the float to float steadily since revolution of the float in a vertical direction is permitted. The solidifying agent retained inside the float serves to solidify the liquid waste.

The solidifying agent could be provided within the container since the float itself is capable of retaining the solidifying agent; subsequently, the solidification of liquid waste inside the container enables the container to be solely and sanitarily disposed.

By controlling a specific gravity of the float to become less than 1, a liquid surface could be easily confirmed from outside by checking the position of the float since the float would always remain afloat at a gas-liquid interface; accordingly, an amount of the absorbed liquid waste could easily be visually recognized and could also function as a level gauge.

By forming the float into a spherical shape, a disc shape, a circular-donut shape, or with an oval shaped cross section in a longitudinal direction, an elliptical cross section in a longitudinal direction, the float could bear a simple structure capable of maintaining a uniform floating state even when revolving in a vertical direction and thus structured, a relatively large capacity of solidifying agent could be retained inside the float.

The float could bear a simple structure where a floating position could be matched to the position of the absorption stop valve arranged at the upper inner portion of the container by forming a guide member at an outer peripheral portion of a float body in which the guide member is restrained by an inner wall of the container for restricting a floating position of the float in a horizontal direction.

By structuring the float to push upward and activate an absorption stop valve arranged at an inner side of an upper portion of the container, the absorption stop valve is activated to automatically stop absorption when the float inside the container reaches an upper end portion of the container; subsequently, the buoyancy of the float activates the absorption stop valve to automatically stop the absorption of liquid waste before the container becomes full and also serves to prevent an air pump or the like from malfunctioning from an excessive absorption into the container.

By wrapping the solidifying agent retained inside the float with a water permeable sheet (e.g. traditional Japanese paper), the liquid waste absorbed from the upper portion flows downward into the container and permeates into the water permeable sheet (e.g. traditional Japanese paper) via the flow path and contacts to the solidifying agent, or in a state where the liquid waste has flowed through and under the float, the liquid waste permeates into the water permeable sheet (e.g. traditional Japanese paper) and contacts to the solidifying agent; and then, the solidifying agent swells to tear the water permeable sheet causing the solidifying agent from the flow path to be mixed into the liquid waste so as to solidify the liquid waste under the float.

By wrapping the solidifying agent retained inside the float with a water-soluble film, the liquid waste absorbed from the upper portion flows downward into the container via the flow path and contacts to the water-soluble sheet and dissolves the water-soluble sheet, or in a state where the liquid waste has flowed through and under the float, the liquid waste contacts to the water-soluble sheet and dissolves the water-soluble sheet causing the solidifying agent from the flow path to be mixed into the liquid waste so as to solidify the liquid waste under the float.

By having at least one portion of the float for a liquid waste disposal apparatus in a florescent color or in a color distinguishable between a color of a liquid waste, a liquid surface could easily be confirmed from outside since the position of the float could easily be visually recognized; accordingly, an operator could positively confirm the used capacity as well as the remaining capacity of the container.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A float for a liquid waste disposal apparatus contained in a floatable state inside a container for containing an absorbed liquid waste, comprising:
   a solidifying agent retained inside; and
   a flow path for flowing downward the liquid waste absorbed from an upper portion into the container;
   wherein the float is permitted to revolve in a vertical direction and the solidifying agent retained inside the float is wrapped inside by a water permeable sheet or a water-soluble film.

2. The float for a liquid waste disposal apparatus according to claim 1, wherein the float has a spherical shape, a disc shape, or a circular-donut shape, or has an oval shaped cross section in a longitudinal direction, or an elliptical cross section in a longitudinal direction.

3. The float for a liquid waste disposal apparatus according to claim 2, wherein the float pushes upward an absorption stop valve arranged at an upper inner portion of the container for activating the absorption stop valve.

4. The float for a liquid waste disposal apparatus according to claim 2, wherein at least one portion of the float is in a florescent color or in a color distinguishable from a color of the liquid waste.

5. The float for a liquid waste disposal apparatus according to claim 1, wherein the float is structured with a guide member arranged at an outer peripheral portion of a float body in which the guide member is restrained at an inner wall of the container for restricting a floating position of the float in a horizontal direction.

6. The float for a liquid waste disposal apparatus according to claim 5, wherein the float pushes upward an absorption stop valve arranged at an upper inner portion of the container for activating the absorption stop valve.

7. The float for a liquid waste disposal apparatus according to claim 5, wherein at least one portion of the float is in a florescent color or in a color distinguishable from a color of the liquid waste.

8. The float for a liquid waste disposal apparatus according to claim 1, wherein the float pushes upward an absorption stop valve arranged at an upper inner portion of the container for activating the absorption stop valve.

9. The float for a liquid waste disposal apparatus according to claim 8, wherein at least one portion of the float is in a florescent color or in a color distinguishable from a color of the liquid waste.

10. The float for a liquid waste disposal apparatus according to claim 1 wherein at least one portion of the float is in a florescent color or in a color distinguishable from a color of the liquid waste.

11. The float for a liquid waste disposal apparatus according to claim 3, wherein at least one portion of the float is in a florescent color or in a color distinguishable from a color of the liquid waste.

* * * * *